(12) United States Patent
Belcher

(10) Patent No.: US 8,170,641 B2
(45) Date of Patent: May 1, 2012

(54) METHOD OF IMAGING AN EXTREMITY OF A PATIENT

(75) Inventor: Nathan E. Belcher, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 459 days.

(21) Appl. No.: 12/389,930

(22) Filed: Feb. 20, 2009

(65) Prior Publication Data

US 2010/0217109 A1    Aug. 26, 2010

(51) Int. Cl.
*A61B 5/00* (2006.01)
(52) U.S. Cl. .................. 600/407; 600/410; 600/425
(58) Field of Classification Search .............. 600/410, 600/407, 414, 416, 420, 425, 426, 430, 436, 600/438, 443
See application file for complete search history.

(56) References Cited

U.S. PATENT DOCUMENTS

| | | | |
|---|---|---|---|
| 1,480,285 A | 1/1924 | Moore | |
| 2,181,746 A | 11/1939 | Siebrandt | |
| 2,407,845 A | 9/1946 | Nemeyer | |
| 2,618,913 A | 11/1952 | Plancon et al. | |
| 2,910,978 A | 11/1959 | Urist | |
| 3,840,904 A | 10/1974 | Tronzo | |
| 4,246,895 A | 1/1981 | Rehder | |
| 4,324,006 A | 4/1982 | Charnley | |
| 4,436,684 A | 3/1984 | White | |
| 4,475,549 A | 10/1984 | Oh | |
| 4,506,393 A | 3/1985 | Murphy | |
| 4,524,766 A | 6/1985 | Petersen | |
| 4,619,658 A | 10/1986 | Pappas et al. | |
| 4,621,630 A | 11/1986 | Kenna | |
| 4,632,111 A | 12/1986 | Roche | |
| 4,633,862 A | 1/1987 | Petersen | |
| 4,663,720 A | 5/1987 | Duret et al. | |
| 4,695,283 A | 9/1987 | Aldinger | |
| 4,703,751 A | 11/1987 | Pohl | |
| 4,704,686 A | 11/1987 | Aldinger | |

(Continued)

FOREIGN PATENT DOCUMENTS

CA    2447694 A1    12/2002
(Continued)

OTHER PUBLICATIONS

"Patient Matched PMI Implants, C.A.M.R.A. 3-D Imaging," brochure, Biomet, Inc. (1990) 6 pages.

(Continued)

*Primary Examiner* — Ruth S Smith
(74) *Attorney, Agent, or Firm* — Harness, Dickey

(57) ABSTRACT

A method of imaging a body part of a patient can include acquiring a first, second and third sets of image data from a first, second and third anatomical reference areas. The first, second and third sets of image data can then be compiled to produce a legend of the body part. The legend can have positional information of the first, second and third anatomical reference areas. A fourth, fifth and sixth sets of image data of the first, second and anatomical reference areas can be acquired. The fourth, fifth and sixth sets of image data can have increased image information relative to the first, second and third sets of image data, respectively. The locations of the fourth, fifth and sixth sets of image data relative to the first, second and third sets of image data can be correlated using the legend to determine a characteristic of the body part.

15 Claims, 3 Drawing Sheets

U.S. PATENT DOCUMENTS

| | | | |
|---|---|---|---|
| 4,721,104 A | 1/1988 | Kaufman et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,030,221 A | 7/1991 | Buechel et al. |
| 5,041,117 A | 8/1991 | Engelhardt |
| 5,053,039 A | 10/1991 | Hofmann et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,129,908 A | 7/1992 | Petersen |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,438,263 A * | 8/1995 | Dworkin et al. | 324/309 |
| 5,440,496 A | 8/1995 | Andersson et al. |
| 5,448,489 A | 9/1995 | Reuben |
| 5,452,407 A | 9/1995 | Crook |
| 5,454,816 A | 10/1995 | Ashby |
| 5,474,559 A | 12/1995 | Bertin et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,620,448 A | 4/1997 | Puddu |
| 5,634,927 A | 6/1997 | Houston et al. |
| 5,658,294 A | 8/1997 | Sederholm |
| 5,677,107 A | 10/1997 | Neckers |
| 5,681,354 A | 10/1997 | Eckhoff |
| 5,682,886 A * | 11/1997 | Delp et al. | 600/407 |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,899,907 A | 5/1999 | Johnson |
| 5,901,060 A | 5/1999 | Schall et al. |
| 5,911,724 A | 6/1999 | Wehrli |
| 5,942,370 A | 8/1999 | Neckers |
| 5,967,777 A | 10/1999 | Klein et al. |
| 5,976,149 A | 11/1999 | Masini |
| 6,033,415 A | 3/2000 | Mittelstadt et al. |
| 6,059,833 A | 5/2000 | Doets |
| 6,120,510 A | 9/2000 | Albrektsson et al. |
| 6,120,544 A | 9/2000 | Grundei et al. |
| 6,126,690 A | 10/2000 | Ateshian et al. |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |
| 6,427,698 B1 | 8/2002 | Yoon |
| 6,459,948 B1 | 10/2002 | Ateshian et al. |
| 6,463,351 B1 | 10/2002 | Clynch |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,554,837 B1 | 4/2003 | Hauri et al. |
| 6,556,008 B2 * | 4/2003 | Thesen | 324/307 |
| 6,558,391 B2 | 5/2003 | Axelson, Jr. et al. |
| 6,558,428 B2 | 5/2003 | Park |
| 6,564,085 B2 * | 5/2003 | Meaney et al. | 600/415 |
| 6,567,681 B1 | 5/2003 | Lindequist |
| 6,575,980 B1 | 6/2003 | Robie et al. |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |

| | | | | | | |
|---|---|---|---|---|---|---|
| 6,716,249 B2 | 4/2004 | Hyde | | 7,896,921 B2 | 3/2011 | Smith et al. |
| 6,725,077 B1 * | 4/2004 | Balloni et al. ............... 600/410 | | 7,935,119 B2 | 5/2011 | Ammann et al. |
| 6,738,657 B1 | 5/2004 | Franklin et al. | | 7,938,861 B2 | 5/2011 | King et al. |
| 6,740,092 B2 | 5/2004 | Lombardo et al. | | 7,963,968 B2 | 6/2011 | Dees, Jr. |
| 6,749,638 B1 | 6/2004 | Saladino | | 2001/0005797 A1 | 6/2001 | Barlow et al. |
| 6,750,653 B1 | 6/2004 | Zou et al. | | 2001/0011190 A1 | 8/2001 | Park |
| 6,772,026 B2 | 8/2004 | Bradbury et al. | | 2002/0007294 A1 | 1/2002 | Bradbury et al. |
| 6,780,190 B2 | 8/2004 | Maroney | | 2002/0059049 A1 | 5/2002 | Bradbury et al. |
| 6,786,930 B2 | 9/2004 | Biscup | | 2002/0082741 A1 | 6/2002 | Mazumder et al. |
| 6,799,066 B2 | 9/2004 | Steines et al. | | 2002/0087274 A1 | 7/2002 | Alexander et al. |
| 6,827,723 B2 | 12/2004 | Carson | | 2002/0128872 A1 | 9/2002 | Giammattei |
| 6,905,514 B2 | 6/2005 | Carignan et al. | | 2002/0147415 A1 | 10/2002 | Martelli |
| 6,923,817 B2 | 8/2005 | Carson et al. | | 2003/0009171 A1 | 1/2003 | Tornier |
| 6,923,831 B2 | 8/2005 | Fell et al. | | 2003/0009234 A1 | 1/2003 | Treacy et al. |
| 6,932,842 B1 | 8/2005 | Litschko et al. | | 2003/0011624 A1 | 1/2003 | Ellis |
| 6,942,475 B2 | 9/2005 | Ensign et al. | | 2003/0018338 A1 | 1/2003 | Axelson et al. |
| 6,944,518 B2 | 9/2005 | Roose | | 2003/0039676 A1 | 2/2003 | Boyce et al. |
| 6,945,976 B2 | 9/2005 | Ball et al. | | 2003/0055502 A1 | 3/2003 | Lang et al. |
| 6,953,480 B2 | 10/2005 | Mears et al. | | 2003/0109784 A1 | 6/2003 | Loh et al. |
| 6,960,216 B2 | 11/2005 | Kolb et al. | | 2003/0158606 A1 | 8/2003 | Coon et al. |
| 6,990,220 B2 | 1/2006 | Ellis et al. | | 2003/0171757 A1 | 9/2003 | Coon et al. |
| 7,029,479 B2 | 4/2006 | Tallarida et al. | | 2003/0216669 A1 | 11/2003 | Lang et al. |
| 7,042,222 B2 | 5/2006 | Zheng et al. | | 2004/0018144 A1 | 1/2004 | Briscoe |
| 7,048,741 B2 | 5/2006 | Swanson | | 2004/0054372 A1 | 3/2004 | Corden et al. |
| 7,050,877 B2 | 5/2006 | Iseki et al. | | 2004/0068187 A1 | 4/2004 | Krause et al. |
| 7,060,074 B2 | 6/2006 | Rosa et al. | | 2004/0092932 A1 | 5/2004 | Aubin et al. |
| 7,074,241 B2 | 7/2006 | McKinnon | | 2004/0098133 A1 | 5/2004 | Carignan et al. |
| RE39,301 E | 9/2006 | Bertin | | 2004/0102852 A1 | 5/2004 | Johnson et al. |
| 7,104,997 B2 | 9/2006 | Lionberger et al. | | 2004/0102866 A1 | 5/2004 | Harris et al. |
| 7,105,026 B2 | 9/2006 | Johnson et al. | | 2004/0106926 A1 | 6/2004 | Leitner et al. |
| 7,115,131 B2 | 10/2006 | Engh et al. | | 2004/0115586 A1 | 6/2004 | Andreiko et al. |
| 7,141,053 B2 | 11/2006 | Rosa et al. | | 2004/0122439 A1 | 6/2004 | Dwyer et al. |
| 7,169,185 B2 | 1/2007 | Sidebotham | | 2004/0128026 A1 | 7/2004 | Harris et al. |
| 7,176,466 B2 | 2/2007 | Rousso et al. | | 2004/0133276 A1 | 7/2004 | Lang et al. |
| 7,184,814 B2 | 2/2007 | Lang et al. | | 2004/0138754 A1 | 7/2004 | Lang et al. |
| 7,198,628 B2 | 4/2007 | Ondrla et al. | | 2004/0143336 A1 | 7/2004 | Burkinshaw |
| 7,218,232 B2 | 5/2007 | DiSilvestro et al. | | 2004/0147927 A1 | 7/2004 | Tsougarakis et al. |
| 7,239,908 B1 | 7/2007 | Alexander et al. | | 2004/0153079 A1 | 8/2004 | Tsougarakis et al. |
| 7,241,315 B2 | 7/2007 | Evans | | 2004/0158254 A1 | 8/2004 | Eisermann |
| 7,255,702 B2 | 8/2007 | Serra et al. | | 2004/0162619 A1 | 8/2004 | Blaylock et al. |
| 7,258,701 B2 | 8/2007 | Aram et al. | | 2004/0167390 A1 | 8/2004 | Alexander et al. |
| 7,275,218 B2 | 9/2007 | Petrella et al. | | 2004/0171924 A1 | 9/2004 | Mire et al. |
| 7,282,054 B2 | 10/2007 | Steffensmeier et al. | | 2004/0172137 A1 | 9/2004 | Blaylock et al. |
| 7,294,133 B2 | 11/2007 | Zink et al. | | 2004/0181144 A1 | 9/2004 | Cinquin et al. |
| 7,297,164 B2 | 11/2007 | Johnson et al. | | 2004/0204644 A1 | 10/2004 | Tsougarakis et al. |
| 7,309,339 B2 | 12/2007 | Cusick et al. | | 2004/0204760 A1 | 10/2004 | Fitz et al. |
| 7,333,013 B2 | 2/2008 | Berger | | 2004/0212586 A1 | 10/2004 | Denny |
| 7,335,231 B2 | 2/2008 | McLean | | 2004/0236424 A1 | 11/2004 | Berez et al. |
| 7,371,260 B2 | 5/2008 | Malinin | | 2004/0243481 A1 | 12/2004 | Bradbury et al. |
| 7,383,164 B2 | 6/2008 | Aram et al. | | 2004/0254584 A1 | 12/2004 | Sarin et al. |
| 7,385,498 B2 | 6/2008 | Dobosz | | 2005/0008887 A1 | 1/2005 | Haymann et al. |
| 7,388,972 B2 | 6/2008 | Kitson | | 2005/0010300 A1 | 1/2005 | Disilvestro et al. |
| 7,392,076 B2 | 6/2008 | Moctezuma de La Barrera | | 2005/0015022 A1 | 1/2005 | Richard et al. |
| 7,427,272 B2 | 9/2008 | Richard et al. | | 2005/0019664 A1 | 1/2005 | Matsumoto |
| 7,468,075 B2 | 12/2008 | Lang et al. | | 2005/0027303 A1 | 2/2005 | Lionberger et al. |
| 7,474,223 B2 | 1/2009 | Nycz et al. | | 2005/0027361 A1 | 2/2005 | Reiley |
| 7,527,631 B2 | 5/2009 | Maroney et al. | | 2005/0043806 A1 | 2/2005 | Cook et al. |
| 7,534,263 B2 | 5/2009 | Burdulis, Jr. et al. | | 2005/0043837 A1 | 2/2005 | Rubbert et al. |
| 7,542,791 B2 | 6/2009 | Mire et al. | | 2005/0049524 A1 | 3/2005 | Lefevre et al. |
| 7,559,931 B2 | 7/2009 | Stone | | 2005/0059873 A1 | 3/2005 | Glozman et al. |
| 7,575,602 B2 | 8/2009 | Amirouche et al. | | 2005/0060040 A1 | 3/2005 | Auxepaules et al. |
| 7,578,851 B2 | 8/2009 | Dong et al. | | 2005/0065628 A1 | 3/2005 | Roose |
| 7,582,091 B2 | 9/2009 | Duncan et al. | | 2005/0070897 A1 | 3/2005 | Petersen |
| 7,591,821 B2 | 9/2009 | Kelman | | 2005/0071015 A1 | 3/2005 | Sekel |
| 7,601,155 B2 | 10/2009 | Petersen | | 2005/0075641 A1 | 4/2005 | Singhatat et al. |
| 7,604,639 B2 | 10/2009 | Swanson | | 2005/0096535 A1 | 5/2005 | de la Barrera |
| 7,611,516 B2 | 11/2009 | Maroney | | 2005/0113841 A1 | 5/2005 | Sheldon et al. |
| 7,618,451 B2 | 11/2009 | Berez et al. | | 2005/0113846 A1 | 5/2005 | Carson |
| 7,621,915 B2 | 11/2009 | Frederick et al. | | 2005/0119664 A1 | 6/2005 | Carignan et al. |
| 7,625,409 B2 | 12/2009 | Saltzman et al. | | 2005/0131662 A1 | 6/2005 | Ascenzi et al. |
| 7,651,501 B2 | 1/2010 | Penenberg et al. | | 2005/0137708 A1 | 6/2005 | Clark |
| 7,682,398 B2 | 3/2010 | Croxton et al. | | 2005/0148843 A1 | 7/2005 | Roose |
| 7,695,477 B2 | 4/2010 | Creger et al. | | 2005/0171545 A1 | 8/2005 | Walsh et al. |
| 7,695,521 B2 | 4/2010 | Ely et al. | | 2005/0203536 A1 | 9/2005 | Laffargue et al. |
| 7,704,253 B2 | 4/2010 | Bastian et al. | | 2005/0203540 A1 | 9/2005 | Broyles |
| 7,794,504 B2 | 9/2010 | Case | | 2005/0216305 A1 | 9/2005 | Funderud |
| 7,806,896 B1 | 10/2010 | Bonutti | | 2005/0222573 A1 | 10/2005 | Branch et al. |
| 7,819,925 B2 | 10/2010 | King et al. | | 2005/0234461 A1 | 10/2005 | Burdulis et al. |
| 7,828,806 B2 | 11/2010 | Graf et al. | | 2005/0234468 A1 | 10/2005 | Carson |

| | | | | | | |
|---|---|---|---|---|---|---|
| 2005/0244239 A1 | 11/2005 | Shimp | | 2007/0276400 A1 | 11/2007 | Moore et al. |
| 2005/0245934 A1 | 11/2005 | Tuke et al. | | 2007/0276501 A1 | 11/2007 | Betz et al. |
| 2005/0245936 A1 | 11/2005 | Tuke et al. | | 2007/0288030 A1 | 12/2007 | Metzger et al. |
| 2005/0267353 A1 | 12/2005 | Marquart et al. | | 2008/0009952 A1 | 1/2008 | Hodge |
| 2005/0267584 A1 | 12/2005 | Burdulis et al. | | 2008/0015605 A1 | 1/2008 | Collazo |
| 2005/0273114 A1 | 12/2005 | Novak | | 2008/0021299 A1 | 1/2008 | Meulink |
| 2005/0283252 A1 | 12/2005 | Coon et al. | | 2008/0021494 A1 | 1/2008 | Schmelzeisen-Redeker et al. |
| 2005/0283253 A1 | 12/2005 | Coon et al. | | 2008/0021567 A1 | 1/2008 | Meulink et al. |
| 2006/0004284 A1 | 1/2006 | Grunschlager et al. | | 2008/0027563 A1 | 1/2008 | Johnson et al. |
| 2006/0015120 A1 | 1/2006 | Richard et al. | | 2008/0033442 A1 | 2/2008 | Amiot et al. |
| 2006/0030853 A1 | 2/2006 | Haines | | 2008/0051910 A1 | 2/2008 | Kammerzell et al. |
| 2006/0038520 A1 | 2/2006 | Negoro et al. | | 2008/0058945 A1 | 3/2008 | Hajaj et al. |
| 2006/0052725 A1 | 3/2006 | Santilli | | 2008/0058947 A1 | 3/2008 | Earl et al. |
| 2006/0058803 A1 | 3/2006 | Cuckler et al. | | 2008/0062183 A1 | 3/2008 | Swaelens |
| 2006/0058884 A1 | 3/2006 | Aram et al. | | 2008/0065225 A1 | 3/2008 | Wasielewski et al. |
| 2006/0058886 A1 | 3/2006 | Wozencroft | | 2008/0112996 A1 | 5/2008 | Harlow et al. |
| 2006/0089621 A1 | 4/2006 | Fard | | 2008/0114370 A1 | 5/2008 | Schoenefeld |
| 2006/0093988 A1 | 5/2006 | Swaelens et al. | | 2008/0133022 A1 | 6/2008 | Caylor |
| 2006/0094951 A1 | 5/2006 | Dean et al. | | 2008/0140209 A1 | 6/2008 | Iannotti et al. |
| 2006/0100832 A1 | 5/2006 | Bowman | | 2008/0146969 A1 | 6/2008 | Kurtz |
| 2006/0111722 A1 | 5/2006 | Bouadi | | 2008/0147072 A1 | 6/2008 | Park et al. |
| 2006/0122616 A1 | 6/2006 | Bennett et al. | | 2008/0161815 A1 | 7/2008 | Schoenefeld et al. |
| 2006/0136058 A1 | 6/2006 | Pietrzak | | 2008/0172125 A1 | 7/2008 | Ek |
| 2006/0142657 A1 | 6/2006 | Quaid et al. | | 2008/0195099 A1 | 8/2008 | Minas |
| 2006/0155380 A1 | 7/2006 | Clemow et al. | | 2008/0195107 A1 | 8/2008 | Cuckler et al. |
| 2006/0161167 A1 | 7/2006 | Myers et al. | | 2008/0195216 A1 | 8/2008 | Philipp |
| 2006/0172263 A1 | 8/2006 | Quadling et al. | | 2008/0200926 A1 | 8/2008 | Verard et al. |
| 2006/0178497 A1 | 8/2006 | Gevaert et al. | | 2008/0208200 A1 | 8/2008 | Crofford |
| 2006/0184177 A1 | 8/2006 | Echeverri | | 2008/0215059 A1 | 9/2008 | Carignan et al. |
| 2006/0190086 A1 | 8/2006 | Clemow et al. | | 2008/0230422 A1 | 9/2008 | Pleil et al. |
| 2006/0195198 A1 | 8/2006 | James | | 2008/0234664 A1 | 9/2008 | May et al. |
| 2006/0204932 A1 | 9/2006 | Haymann et al. | | 2008/0234683 A1 | 9/2008 | May |
| 2006/0210644 A1 | 9/2006 | Levin | | 2008/0234685 A1 | 9/2008 | Gjerde |
| 2006/0235421 A1 | 10/2006 | Rosa et al. | | 2008/0234833 A1 | 9/2008 | Bandoh et al. |
| 2006/0271058 A1 | 11/2006 | Ashton et al. | | 2008/0243127 A1 | 10/2008 | Lang et al. |
| 2006/0276796 A1 | 12/2006 | Creger et al. | | 2008/0255674 A1 | 10/2008 | Rahaman et al. |
| 2006/0276797 A1 | 12/2006 | Botimer | | 2008/0257363 A1 | 10/2008 | Schoenefeld et al. |
| 2006/0287733 A1 | 12/2006 | Bonutti | | 2008/0262624 A1 | 10/2008 | White et al. |
| 2007/0015995 A1 | 1/2007 | Lang et al. | | 2008/0269906 A1 | 10/2008 | Iannotti et al. |
| 2007/0016209 A1 | 1/2007 | Ammann et al. | | 2008/0275452 A1 | 11/2008 | Lang et al. |
| 2007/0027680 A1 | 2/2007 | Ashley et al. | | 2008/0281328 A1 | 11/2008 | Lang et al. |
| 2007/0066917 A1 | 3/2007 | Hodorek et al. | | 2008/0281329 A1 | 11/2008 | Fitz et al. |
| 2007/0073137 A1 | 3/2007 | Schoenefeld | | 2008/0281426 A1 | 11/2008 | Fitz et al. |
| 2007/0083214 A1 | 4/2007 | Duncan et al. | | 2008/0287954 A1 | 11/2008 | Kunz et al. |
| 2007/0083266 A1 | 4/2007 | Lang | | 2008/0294266 A1 | 11/2008 | Steinberg |
| 2007/0100258 A1 | 5/2007 | Shoham et al. | | 2008/0300600 A1 | 12/2008 | Guelat et al. |
| 2007/0100462 A1 | 5/2007 | Lang et al. | | 2008/0306558 A1 | 12/2008 | Hakki |
| 2007/0118055 A1 | 5/2007 | McCombs | | 2008/0312659 A1 | 12/2008 | Metzger et al. |
| 2007/0118243 A1 | 5/2007 | Schroeder et al. | | 2008/0319448 A1 | 12/2008 | Lavallee et al. |
| 2007/0150068 A1 | 6/2007 | Dong et al. | | 2009/0012526 A1 | 1/2009 | Fletcher |
| 2007/0156066 A1 | 7/2007 | McGinley et al. | | 2009/0018546 A1 | 1/2009 | Daley |
| 2007/0156171 A1 | 7/2007 | Lang et al. | | 2009/0018666 A1 | 1/2009 | Grundei et al. |
| 2007/0162038 A1 | 7/2007 | Tuke | | 2009/0024131 A1 | 1/2009 | Metzger et al. |
| 2007/0162039 A1 | 7/2007 | Wozencroft | | 2009/0043556 A1 | 2/2009 | Axelson et al. |
| 2007/0173946 A1 | 7/2007 | Bonutti | | 2009/0076371 A1 | 3/2009 | Lang et al. |
| 2007/0185498 A2 | 8/2007 | Lavallee | | 2009/0076512 A1 | 3/2009 | Ammann et al. |
| 2007/0191962 A1 | 8/2007 | Jones et al. | | 2009/0082770 A1 | 3/2009 | Worner et al. |
| 2007/0198022 A1 | 8/2007 | Lang et al. | | 2009/0087276 A1 | 4/2009 | Rose |
| 2007/0203430 A1 | 8/2007 | Lang et al. | | 2009/0088674 A1 | 4/2009 | Caillouette et al. |
| 2007/0203605 A1 | 8/2007 | Melton et al. | | 2009/0088753 A1 | 4/2009 | Aram et al. |
| 2007/0219639 A1 | 9/2007 | Otto et al. | | 2009/0088754 A1 | 4/2009 | Aker et al. |
| 2007/0219640 A1 | 9/2007 | Steinberg | | 2009/0088755 A1 | 4/2009 | Aker et al. |
| 2007/0226986 A1 | 10/2007 | Park et al. | | 2009/0088758 A1 | 4/2009 | Bennett |
| 2007/0233121 A1 | 10/2007 | Carson et al. | | 2009/0088759 A1 | 4/2009 | Aram et al. |
| 2007/0233136 A1 | 10/2007 | Wozencroft | | 2009/0088760 A1 | 4/2009 | Aram et al. |
| 2007/0233140 A1 | 10/2007 | Metzger et al. | | 2009/0088761 A1 | 4/2009 | Roose et al. |
| 2007/0233141 A1 | 10/2007 | Park et al. | | 2009/0088763 A1 | 4/2009 | Aram et al. |
| 2007/0233269 A1 | 10/2007 | Steines et al. | | 2009/0088865 A1 | 4/2009 | Brehm |
| 2007/0233272 A1 | 10/2007 | Boyce et al. | | 2009/0088866 A1 | 4/2009 | Case |
| 2007/0238069 A1 | 10/2007 | Lovald et al. | | 2009/0089034 A1 | 4/2009 | Penney et al. |
| 2007/0239282 A1 | 10/2007 | Caylor et al. | | 2009/0089081 A1 | 4/2009 | Haddad |
| 2007/0239481 A1 | 10/2007 | DiSilvestro et al. | | 2009/0093816 A1 | 4/2009 | Roose et al. |
| 2007/0250169 A1 | 10/2007 | Lang | | 2009/0096613 A1 | 4/2009 | Westrick |
| 2007/0253617 A1 | 11/2007 | Arata et al. | | 2009/0099567 A1 | 4/2009 | Zajac |
| 2007/0255288 A1 | 11/2007 | Mahfouz et al. | | 2009/0105837 A1 | 4/2009 | Lafosse et al. |
| 2007/0255412 A1 | 11/2007 | Hajaj et al. | | 2009/0118736 A1 | 5/2009 | Kreuzer |
| 2007/0262867 A1 | 11/2007 | Westrick et al. | | 2009/0131941 A1 | 5/2009 | Park et al. |
| 2007/0272747 A1 | 11/2007 | Woods et al. | | 2009/0131942 A1 | 5/2009 | Aker et al. |
| 2007/0276224 A1 | 11/2007 | Lang et al. | | 2009/0138020 A1 | 5/2009 | Park et al. |

| | | | |
|---|---|---|---|
| 2009/0149965 A1 | 6/2009 | Quaid | |
| 2009/0149977 A1 | 6/2009 | Schendel | |
| 2009/0151736 A1 | 6/2009 | Belcher et al. | |
| 2009/0157083 A1 | 6/2009 | Park et al. | |
| 2009/0163922 A1 | 6/2009 | Meridew et al. | |
| 2009/0163923 A1 | 6/2009 | Flett et al. | |
| 2009/0164024 A1 | 6/2009 | Rudan et al. | |
| 2009/0177282 A1 | 7/2009 | Bureau et al. | |
| 2009/0187193 A1 | 7/2009 | Maroney et al. | |
| 2009/0209884 A1 | 8/2009 | Van Vorhis et al. | |
| 2009/0209961 A1 | 8/2009 | Ferrante et al. | |
| 2009/0222014 A1 | 9/2009 | Bojarski et al. | |
| 2009/0222015 A1 | 9/2009 | Park et al. | |
| 2009/0222016 A1 | 9/2009 | Park et al. | |
| 2009/0228016 A1 | 9/2009 | Alvarez et al. | |
| 2009/0234360 A1 | 9/2009 | Alexander | |
| 2009/0248044 A1 | 10/2009 | Amiot et al. | |
| 2009/0254093 A1 | 10/2009 | White et al. | |
| 2009/0254367 A1 | 10/2009 | Belcher et al. | |
| 2009/0270868 A1 | 10/2009 | Park et al. | |
| 2009/0274350 A1 | 11/2009 | Pavlovskaia et al. | |
| 2009/0306676 A1 | 12/2009 | Lang et al. | |
| 2009/0307893 A1 | 12/2009 | Burdulis, Jr. et al. | |
| 2009/0318836 A1 | 12/2009 | Stone et al. | |
| 2010/0016984 A1 | 1/2010 | Trabish | |
| 2010/0016986 A1 | 1/2010 | Trabish | |
| 2010/0023015 A1 | 1/2010 | Park | |
| 2010/0030231 A1 | 2/2010 | Revie et al. | |
| 2010/0042105 A1 | 2/2010 | Park et al. | |
| 2010/0049195 A1 | 2/2010 | Park et al. | |
| 2010/0076439 A1 | 3/2010 | Hatch | |
| 2010/0076505 A1 | 3/2010 | Borja | |
| 2010/0076563 A1 | 3/2010 | Otto et al. | |
| 2010/0076571 A1 | 3/2010 | Hatch | |
| 2010/0082034 A1 | 4/2010 | Remia | |
| 2010/0082035 A1 | 4/2010 | Keefer | |
| 2010/0087829 A1 | 4/2010 | Metzger et al. | |
| 2010/0094295 A1 | 4/2010 | Schnieders et al. | |
| 2010/0105011 A1 | 4/2010 | Karkar et al. | |
| 2010/0121335 A1 | 5/2010 | Penenberg et al. | |
| 2010/0137869 A1 | 6/2010 | Borja et al. | |
| 2010/0137924 A1 | 6/2010 | Tuke et al. | |
| 2010/0145343 A1 | 6/2010 | Johnson et al. | |
| 2010/0145344 A1 | 6/2010 | Jordan et al. | |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |
| 2010/0168857 A1 | 7/2010 | Hatch | |
| 2010/0179663 A1 | 7/2010 | Steinberg | |
| 2010/0185202 A1 | 7/2010 | Lester et al. | |
| 2010/0191244 A1 | 7/2010 | White et al. | |
| 2010/0212138 A1 | 8/2010 | Carroll et al. | |
| 2010/0217109 A1 | 8/2010 | Belcher | |
| 2010/0217270 A1 | 8/2010 | Polinski et al. | |
| 2010/0217338 A1 | 8/2010 | Carroll et al. | |
| 2010/0228257 A1 | 9/2010 | Bonutti | |
| 2010/0249657 A1 | 9/2010 | Nycz et al. | |
| 2010/0249796 A1 | 9/2010 | Nycz | |
| 2010/0262150 A1 | 10/2010 | Lian | |
| 2010/0274253 A1 | 10/2010 | Ure | |
| 2010/0281678 A1 | 11/2010 | Burdulis, Jr. et al. | |
| 2010/0286700 A1 | 11/2010 | Snider et al. | |
| 2010/0292743 A1 | 11/2010 | Singhal et al. | |
| 2010/0305574 A1 | 12/2010 | Fitz et al. | |
| 2010/0324692 A1 | 12/2010 | Uthgenannt et al. | |
| 2011/0004317 A1 | 1/2011 | Hacking et al. | |
| 2011/0015636 A1 | 1/2011 | Katrana et al. | |
| 2011/0015639 A1 | 1/2011 | Metzger et al. | |
| 2011/0029091 A1 | 2/2011 | Bojarski et al. | |
| 2011/0029116 A1 | 2/2011 | Jordan et al. | |
| 2011/0046735 A1 | 2/2011 | Metzger et al. | |
| 2011/0054478 A1 | 3/2011 | Vanasse et al. | |
| 2011/0066193 A1 | 3/2011 | Lang et al. | |
| 2011/0071528 A1 | 3/2011 | Carson | |
| 2011/0071529 A1 | 3/2011 | Carson | |
| 2011/0071530 A1 | 3/2011 | Carson | |
| 2011/0071532 A1 | 3/2011 | Carson | |
| 2011/0071533 A1 | 3/2011 | Metzger et al. | |
| 2011/0092804 A1 | 4/2011 | Schoenefeld et al. | |
| 2011/0093086 A1 | 4/2011 | Witt et al. | |
| 2011/0151027 A1 | 6/2011 | Clineff et al. | |
| 2011/0151259 A1 | 6/2011 | Jarman-Smith et al. | |
| 2011/0153025 A1 | 6/2011 | McMinn | |
| 2011/0190901 A1 | 8/2011 | Weissberg et al. | |
| 2011/0257657 A1 | 10/2011 | Turner et al. | |

FOREIGN PATENT DOCUMENTS

| | | |
|---|---|---|
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| EP | 0114505 A1 | 8/1984 |
| EP | 0326768 A2 | 8/1989 |
| EP | 0579868 A2 | 1/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1437102 A1 | 7/2004 |
| EP | 01486900 A1 | 12/2004 |
| EP | 1852072 A2 | 7/2007 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2007041375 A2 | 4/2007 |
| WO | WO-2007053572 A2 | 5/2007 |

| WO | WO-2007062079 | A2 | 5/2007 |
| WO | WO-2007092841 | A2 | 8/2007 |
| WO | WO-2007137327 | A1 | 12/2007 |
| WO | WO-2007145937 | A2 | 12/2007 |
| WO | WO-2008014618 | A1 | 2/2008 |
| WO | WO-2008021494 | A2 | 2/2008 |
| WO | WO-2008040961 | A1 | 4/2008 |
| WO | WO-2008044055 | A1 | 4/2008 |
| WO | WO-2008101090 | A2 | 8/2008 |
| WO | WO-2008112996 | A1 | 9/2008 |
| WO | WO-2008140748 | A1 | 11/2008 |
| WO | WO-2009001083 | A1 | 12/2008 |
| WO | WO-2009025783 | A1 | 2/2009 |

OTHER PUBLICATIONS

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Chart P., Technical Report: DeVIDE—The Delft Visualisation and Image processing Development Environment, pp. 1-49 (May 31, 2006).

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazan, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability for PCT/US2007/013223 issued Nov. 26, 2007.

International Search Report and Written Opinion for PCT/US2007/013223 mailed Nov. 26, 2007.

International Search Report and Written Opinion for PCT/US2009/039507 mailed Jul. 14, 2009.

International Search Report and Written Opinion for PCT/US2009/039578 mailed Jul. 31, 2009.

International Search Report and Written Opinion for PCT/US2009/056670 mailed Mar. 2, 2010 claiming benefit of U.S. Appl. No. 12/211,407, filed Sep. 16, 2008 (which is a CIP of U.S. Appl. No. 12/039,849, filed Feb. 29, 2008, which is a CIP of U.S. Appl. No. 11/971,390, filed Jan. 9, 2008, which is a CIP of U.S. Appl. No. 11/756,957, filed May 31, 2007).

International Search Report and Written Opinion mailed Apr. 22, 2010 for PCT/US2010/024579 claiming benefit of U.S. Appl. No. 12/389,930, filed Feb. 20, 2009.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796& ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Kelly, Todd C., M.D., "Role of Navigation in Total Hip Arthroplasty." The Journal of Bone & Joint Surgery(2009) pp. 153-158. vol. 91-A, Supplement 1.

Murphy, S.B., et al. "The Hip Sextant: Navigation of Acetabular Component Orientation Using a Mechanical Instrument," brochure. (2009) 1 page.

Radermacher, Klaus, et al. "Computer Assisted Orthopaedic Individual Templates." Clinical Orthopaedics and Related Research. (Sep. 1998) No. 354; pp. 28-38.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

* cited by examiner

METHOD OF IMAGING AN EXTREMITY OF A PATIENT

FIELD

The present disclosure relates to medical imaging such as magnetic resonance imaging (MRI), and, more particularly, relates to a method for imaging a limb of a patient to determine characteristics of a bone or joint.

BACKGROUND

The statements in this section merely provide background information related to the present disclosure and may not constitute prior art.

Anatomical imaging is often performed prior to surgical procedures. MRI, CT or x-ray is often performed, for instance, before implantation of a prosthetic joint, such as a knee joint. The MRI, CT or x-ray image illustrates the joint, allowing doctors to study the joint prior to surgery. Furthermore, cut guides and/or anatomically matching instrumentation can be generated according to the images. As such, the components of the prosthetic device are more likely to be properly aligned, thereby improving comfort and performance for the patient, decreasing wear of the prosthetic components, and increasing longevity of the components.

In the case of a knee joint, it can be preferable for the reconstructed knee to fulfill a number of anatomical relationships. For instance, the mechanical axis of the leg, which extends from the center of the femoral head (i.e., the acetabulum head of the femur) to the center of the ankle, should pass through the middle of the knee joint. The axis of the femur should be inclined at a predetermined "valgus" angle (e.g., 7 degrees) with the mechanical axis of the leg. Furthermore, the axis of the tibia should be collinear with the mechanical axis of the leg. In addition, the mechanical axis of the leg, the axis of the femur, and the axis of the tibia should lie in a common plane when the leg is straightened. MRI, CT, x-ray or fluoroscopic imaging helps in analyzing the knee joint and to plan for surgery to repair the knee joint in order that the prosthesis achieves these and other relationships. More specifically, the MRI, CT, x-ray or fluoroscopic image can help in designing cut guides and planning other surgical procedures such that forces in the leg are transferred through the prosthetic components along the mechanical axis of the leg, from the center of the femoral head, through the middle of the knee joint, and to the ankle.

In the case of a knee joint prosthesis, an MRI, CT, x-ray or fluoroscopic image is often taken of multiple areas of the leg. More specifically, an MRI, CT or fluoroscopic image is taken of the knee joint where the prosthetic components will be implanted. Separate images may be generated for areas spaced away from the knee joint as well. For instance, images are generated for the hip and/or the ankle in order to obtain a more complete analysis of the leg and to locate the centers of the hip joint and ankle joint.

However, this type of imaging can take a long time and can be a complex process. Specifically, in the case of MRI, the patient is positioned in an MRI system, an MRI imaging coil is placed over the target area of the body, and the MRI image is taken of that target area. Then, the body is moved to align the next target area of the body with the MRI imaging coil, and another MRI image is taken. Thus, in the above examples, the knee, hip and ankle are imaged separately. Several MRIs may be necessary, and if the patient moves, the images may be degraded.

SUMMARY

A method of imaging a body part of a patient can include, locating a first anatomical reference area of the body part. A second anatomical reference area of the body part can then be located. A third anatomical reference area of the body part can be located, the second anatomical reference area being generally between the first and third anatomical reference areas. A first, second and third set of image data from the first, second and third anatomical reference areas can be acquired. The first, second and third sets of image data can then be compiled to produce a legend or map of the body part. The map can have positional information of the first, second and third anatomical reference areas relative to each other. Fourth, fifth and sixth sets of image data of the first, second and third body parts, respectively can be acquired. The fourth, fifth and sixth sets of image data can have increased image information relative to the first, second and third sets of image data, respectively. The locations of the fourth, fifth and sixth set of image data relative to the first, second and third sets of image data can be correlated using the map. A characteristic of the body part can then be determined based on the correlation.

According to other features, acquiring the first, second and third sets of image data can include acquiring only ten or less images for each of the first, second and third sets of image data. In other features, a localizer scan is performed on each of the first, second and third anatomical reference areas prior to acquiring the first, second and third sets of image data. According to other features, the fifth set of image data is a bulk image scan of the second anatomical reference area comprising a greater quantity of image scans as compared to corresponding image scans acquired with the second set of image data. The fourth and sixth set of image scans each comprise a greater quantity of image scans as compared to the image scans acquired with the first and third sets of image data, respectively. The first, second and third anatomical reference areas can include an ankle, knee and hip respectively.

According to other features, the patient can be secured to a table, such that the patient's first, second and third anatomical reference areas are immobilized relative to the table during the acquiring of the first, second and third sets of image data. According to the present teachings, the patient can move relative to the table between the acquiring of the third and fourth sets of image data. Similarly, the patient is free to move relative to the table between the acquiring of the fourth and fifth sets of image data and the patient is free to move relative to the table between the acquiring of the fifth and sixth sets of image data.

Further areas of applicability will become apparent from the description provided herein. It should be understood that the description and specific examples are intended for purposes of illustration only and are not intended to limit the scope of the present disclosure. For example, the described method is not limited to solely the knee joint.

DRAWINGS

The drawings described herein are for illustration purposes only and are not intended to limit the scope of the present disclosure in any way.

DETAILED DESCRIPTION

Figure 1:
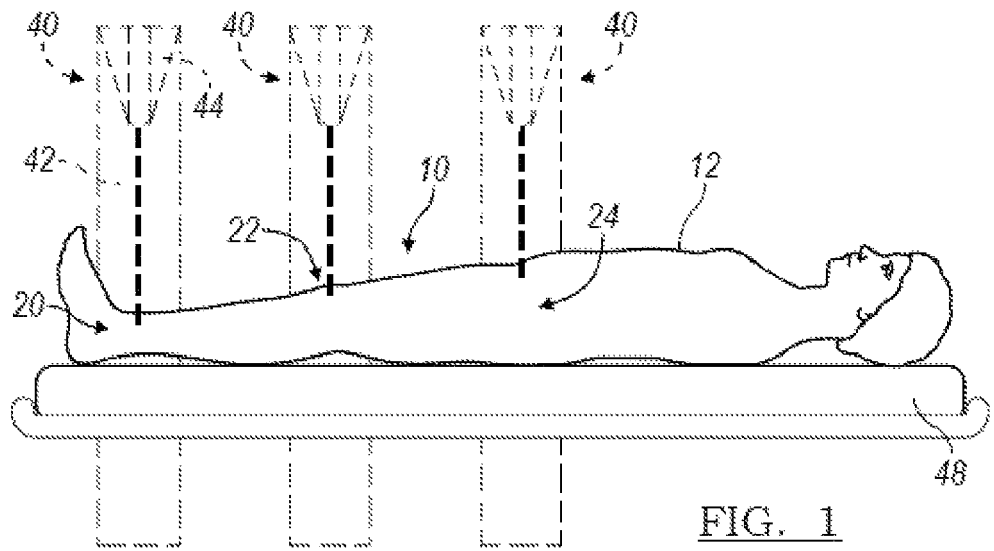
FIG. 1 is a side perspective view of a patient and an exemplary MRI system.

The following description is merely exemplary in nature and is not intended to limit the present disclosure, application, or uses. It should be understood that throughout the drawings, corresponding reference numerals indicate like or corresponding parts and features. It will be appreciated that while specific reference is made to first, second, third, fourth, fifth and sixth scans, these terms do not necessarily refer to a predetermined sequence or number of events and that these scans may be performed in various sequential orders. Furthermore, while the following discussion is directed to MRI imaging, other imaging such as, but not limited to, CT or X-ray imaging may be used.

As will be discussed, the method according to the present teachings can be used for indicating features of a body part, such as a knee joint of a leg. With initial reference to FIGS. 1 and 2, the present method will be described in the context of a leg 10 of a patient 12. It is appreciated that the following teachings are applicable to other body parts or joint axis, such as, but not limited to, an elbow joint of an arm. At the outset, a medical technician identifies a first anatomical reference area 14, a second anatomical reference area 16 and a third anatomical reference area 18. In the present example, the first, second and third anatomical reference areas 14, 16 and 18, correspond to an ankle joint 20, a knee joint 22 and a hip joint 24, respectively.

Referring now to FIGS. 1-4, a method of imaging the knee joint 22 according to the present teachings will be described. In some embodiments of the present method, an initial localizer scan is performed for each of the first, second and third anatomical reference areas 14, 16 and 18, respectively. As is known in the art, a localizer scan can be used to determine structural information about the scanned reference area. Spatial locations of the respective ankle joint 20, knee joint 22 and hip joint 24 relative to each other can be determined, such that subsequent scans (as will be described) will be taken at the correct location. In one example, prior to performing the localizer scans, a center point 30, 32 and 34 of each of the ankle joint 20, knee joint 22 and hip joint 24 can be determined. It will be understood that the center point 32 of the knee joint 22 will coincide with the joint line of the knee, and thus by locating the center point 32 of the knee joint 22, the joint line of the knee can be located. The center points 30 and 32 can also be marked on the patient's skin for future reference.

Next, localizer scans can be performed at the first, second and third anatomical reference areas 14, 16 and 18, such as at the center points 30, 32 and 34 of the respective ankle joint 20, knee joint 22 and hip joint 24. The localizer scans can be performed using an MRI system 40 (FIG. 1). In one example, the ankle joint 20 can be positioned relative to the imaging coil 42. An MRI emitter 44 can then be energized to acquire a localizer image or images of the ankle joint 20. Next, the knee joint 22 can be positioned relative to the imaging coil 42, the MRI emitter 44 energized, and a localizer image or images of the knee joint 22 can be acquired. Next, the hip joint 24 can be positioned relative to the imaging coil 42, the MRI emitter 44 energized, and a localizer image or images of the hip joint 24 can be acquired. It will be understood that while the patient 12 has been illustrated in FIG. 1 resting on a table 48 and the MRI system 40 is shown as three distinct illustrations, it is appreciated that the MRI system 40 can comprise a single unit and the table 48 can be configured to move horizontally through the imaging coil 42, such that sequential images of the ankle joint 20, knee joint 22 and hip joint 24 can be acquired from one MRI system 40.

It will also be understood that the leg of the patient 12 should remain still relative to the table 48 during the entire sequence of conducting localizer scans of the ankle joint 20, knee joint 22 and hip joint 24.

Figure 3:
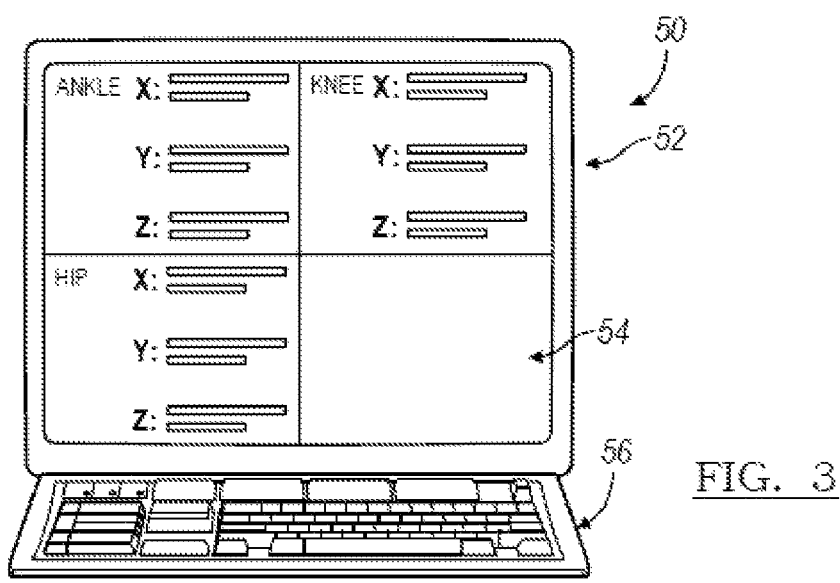
FIG. 3 is a front perspective view of an exemplary work station used during acquisition of image data by the MRI system of FIG. 1.

As illustrated in FIG. 3, the respective localizer scans can be sent to a work station 50. The work station 50 can facilitate the display of localizer scan information 52 onto a display device 54. In some examples, a user interface 56 can be provided that allows a physician or medical technician to provide inputs to control the MRI system 40. Once the localizer scans have been performed, the localizer scan information 52 can be used to determine the spatial relationship between the respective ankle joint 20, knee joint 22 and hip joint 24. This information can be used to determine, for example, how far horizontally the table 48 must translate between the following scans that are performed of the ankle joint 20, knee joint 22 and hip joint 24.

Figure 2:
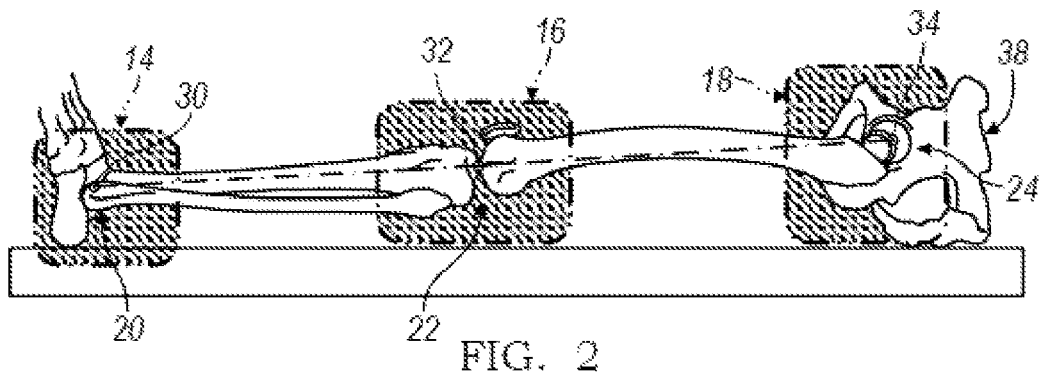
FIG. 2 is a lateral view of the patient's ankle joint, knee joint and hip joint.
Figure 4:
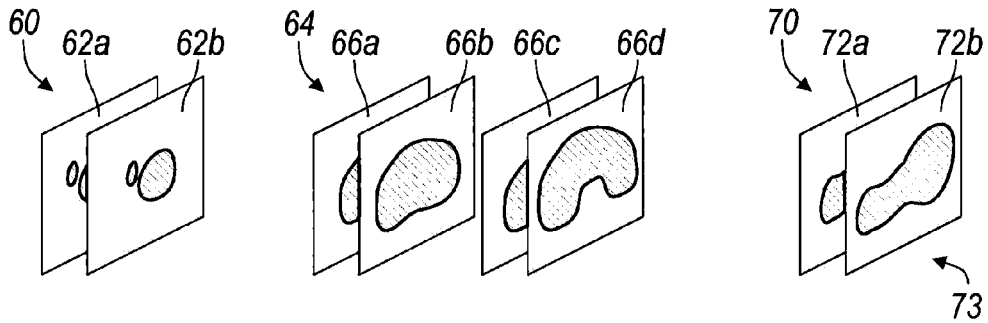
FIG. 4 is a perspective pictorial representation of image data sets taken at the ankle joint, knee joint and hip joint of the patient of FIG. 1.

With specific reference now to FIGS. 1, 2 and 4, creation of a legend or map of the leg 10 according to the present teachings will be described. The ankle joint 20 is positioned relative to the imaging coil 42, and the MRI emitter 44 energized while the patient 12 remains immobile relative to the table 48 to produce a first image data set 60 (FIG. 4) of the ankle joint 20 (i.e., at the first anatomical reference area 14). According to the present teachings, the first image data set 60 can be a series of planar images or slices 62A, 62B each taken through an identified plane of the ankle joint 20. While the image slices 62A and 62B are shown in the axial plane, image slices through other planes such as the sagittal plane or coronal plane may be acquired. In other examples, the first image data set 60 can be a series of planar images taken through non-parallel planes (i.e., any combination of images through the axial, sagittal or coronal planes) of the ankle joint 20. According to the present teachings, the first series of slices 62A, 62B can be a minimal amount of slices, such as less than ten slices for example. While only two slices are shown in FIG. 4 associated with the ankle joint 20, it is appreciated that additional or fewer slices may be acquired.

Next, the knee joint 22 of the patient 12 is aligned with the imaging coil 42 and MRI emitter 44 while the patient 12 remains immobile relative to the table 48. The MRI emitter 44 is energized to produce a second image data set 64 of the knee joint 22 (i.e., the second anatomical reference area 16). According to the present teachings, the second image data set 64 can be a series of planar images or slices 66A, 66B, 66C and 66D. In one example, the slices 66A and 66B can be taken through the tibia and the slices 66C and 66D can be taken through the femur. Again, as described above, the image slices 66A, 66B, 66C and 66D can comprise any combination of image slices taken through the axial, sagittal or coronal planes. In this way, the second image data set 64 can be a series of planar images taken through non-parallel planes of the knee joint 22. According to the present teachings, the second series of slices 66A, 66B, 66C and 66D can be a minimal amount of slices, such as less than ten slices for example. While only four slices are shown in FIG. 4, it is appreciated that additional or fewer slices may be acquired.

Next, the hip joint 24 of the patient 12 is within the field of view of the imaging coil 42 and the MRI emitter 44. Again, the patient 12 is immobilized relative to the table 44. The MRI emitter 44 is then energized to produce a third image data set 70 of the hip joint 24 (i.e., the third anatomical reference area 18). According to the present teachings, the third image data set 70 can be a series of planar images or slices 72A and 72B, each taken through the axial plane of the hip joint 22 or any combination of the axial, sagittal or coronal planes. In this way, the third image data set can be a series of planar images taken through non-parallel planes of the hip joint 24. According to the present teachings, the third series of slices 72A and 72B can be a minimal amount of slices, such as less than ten slices for example. While only two slices are shown in FIG. 4 at the hip joint 24, it is appreciated that additional or fewer slices may be acquired. Again, it will be understood that the patient 12 is immobilized through the entire sequence of acquisition of all the first, second and third image data sets 60, 64 and 70. Because only a minimal amount of image slices are taken to acquire the first, second and third image data sets 60, 64 and 70, the patient 12 is only required to remain still for a relatively short period of time. Once the scans have been completed, the patient 12 is now free to move from the table 48 if desired.

With the respective first, second and third image data sets 60, 64 and 70, a medical technician can use the work station 50 to determine the location of the respective ankle joint 20, knee joint 22 and hip joint 24 relative to each other. This information (i.e., the first, second and third data sets 60, 64 and 70) can be utilized collectively to create a legend or map 73 for a medical technician to correlate more detailed image scans that can be acquired subsequently as will be described.

Figure 5:
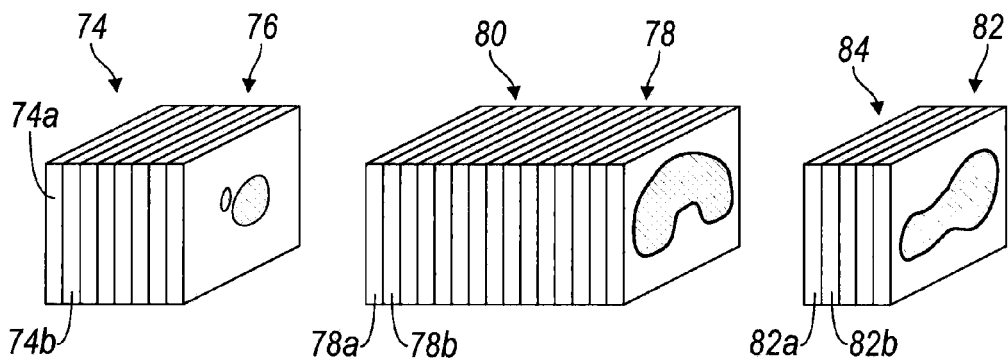
FIG. 5 is a perspective pictorial representation of detailed scans taken of the ankle joint, knee joint and hip joint of the patient of FIG. 1.

Once the legend 73 has been created, the patient 12 returns to the table 48 for acquisition of a detail scan for one of the ankle joint 20, knee joint 22 or hip joint 24. In one example, to acquire a detail scan, the imaging coil 42 of the MRI system 40 is aligned with the ankle joint 20 and a detail scan 74 (FIG. 5) is performed to create a fourth image data set 76 of the ankle joint 20. The ankle detail scan 74 can comprise acquisition of a series of image slices (74A, 74B . . . 74X). As can be appreciated, the fourth image data set 76 has more image slices and therefore increased image information relative to the first image data set 60. Once the fourth image data set 76 has been acquired, the patient 12 is able to move relative to the table 48 if desired. Once it is time for the next image data acquisition, the patient 12 is immobilized relative to the table 48. Next, the knee joint 22 is aligned with the imaging coil 42 and MRI emitter 44. The MRI emitter 44 is then energized to produce a high resolution knee detail scan 78 and a fifth image data set 80 of the knee joint 24. The high resolution knee scan 78 can comprise acquisition of a series of image slices 78A, 78B . . . 78X. According to one example of the present teachings, instead of using the imaging coil 42 and MRI emitter 44, a send/receive coil can be used to acquire the detail scan of the knee joint 22 (and/or the ankle joint 20, and/or the hip joint 24).

Once the high resolution knee detail scan 78 has been acquired, the patient 12 is again free to move relative to the table 48. Once it is time to acquire the next image data set, the patient 12 is immobilized relative to the table 48. The hip joint 24 of the patient 12 is then aligned with the imaging coil 42 of the MRI emitter 44 and a hip detail scan 82 is performed to create a sixth image data set 84. The hip detail scan 82 can comprise acquisition of a series of image slices 82A, 82B . . . 82X. Once acquisition of the hip detail scan 82 has been completed, the image scanning is completed and the patient 12 is then free to move away from the table 48.

Figure 6:
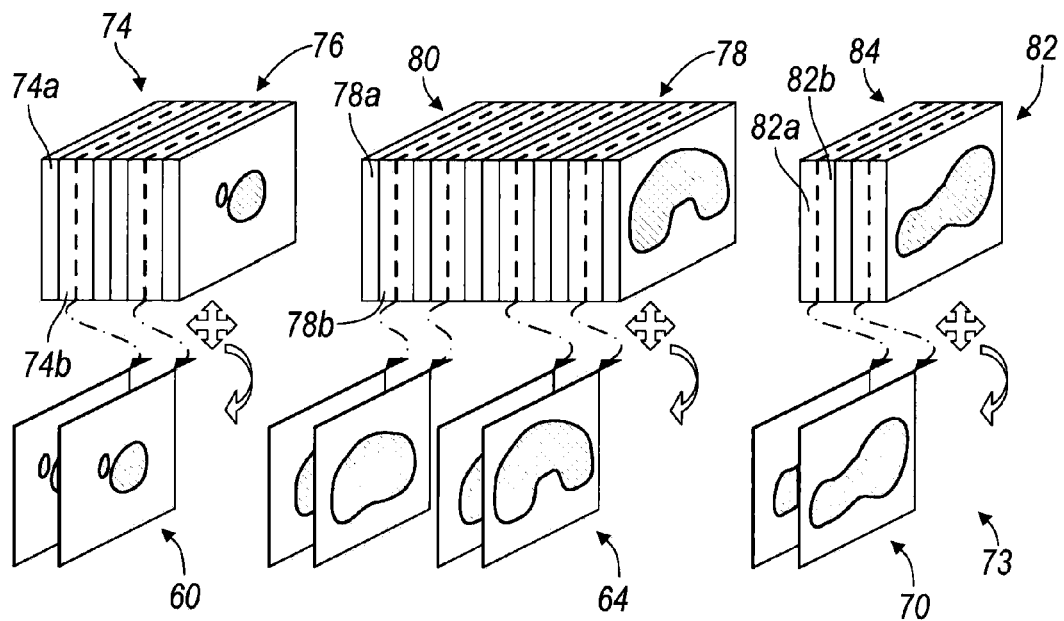
FIG. 6 is a pictorial representation of the detailed data sets taken in FIG. 5 and being correlated with the legend generated from the scans taken in FIG. 4.

Turning now to FIG. 6, using the work station 50, a medical technician will be able to correlate the locations of the fourth, fifth and sixth set of image data 76, 80 and 84 of the respective ankle joint 20, knee joint 22, and hip joint 24 relative to the first image data set 60, second image data set 64 and third image data set 70, respectively. Explained further, since the first, second and third image data sets 60, 64 and 70 are acquired when the ankle joint 20, knee joint 22 and hip joint 24 are all fixed relative to each other, the position of each of the ankle joint 20, knee joint 22 and hip joint 24 relative to each other is known. Because of this relationship between the first, second and third image data sets 60, 64 and 70, the fourth, fifth and sixth image data sets 76, 80 and 84 can be related to the first, second and third image data sets 60, 64 and 70 independently. For example, the fourth image data set 76 can be compared to the first image data set 60 and since the second and third image data sets 60 and 64 were acquired while the knee joint 22 and hip joint 24 were fixed relative to the ankle joint 20, the positional relationship of the fourth image data set 76 relative to the second and third image data sets 64 and 70 is also known.

Thus, by first creating the legend or map 73 of the patient's leg 10, subsequent scans (the fourth, fifth and sixth image data sets 76, 80 and 84) can be overlaid (FIG. 6) and placed in the proper location/orientation. This can allow movement of the patient 12 relative to the table 48 between scans (i.e., the fourth and fifth scans 74 and 78 and the fifth and sixth scans 78 and 82) and while only requiring the patient 12 to remain still for shorter separate periods of time (the time required during the entire sequence of acquisition of the first, second and third image data sets 60, 64 and 70 and the individual time needed for acquisition of the fourth, fifth and sixth image data sets 76, 80 and 84).

Figure 7:
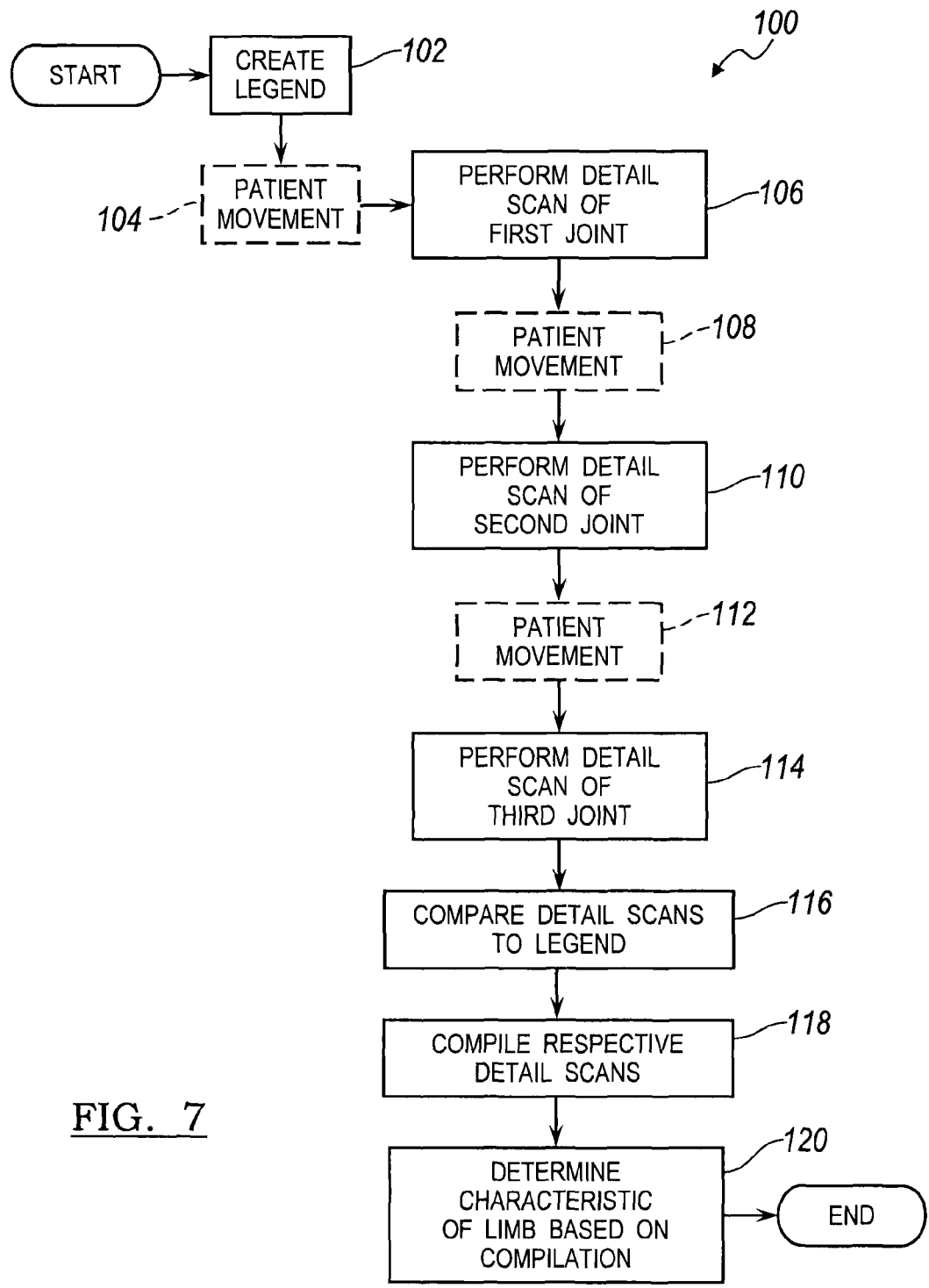
FIG. 7 is an exemplary method of imaging a body part according to the present teachings.

With reference now to FIG. 7, one exemplary method of imaging a body part of a patient 12 is shown and generally identified at reference numeral 100. In block 102, the legend or map 73 is created using the first, second and third image data sets 60, 64 and 70 to create a map of the patient's leg, including relative locations of the ankle joint 20, knee joint 22 and hip joint 24. Once the legend 73 has been created in block 102, the patient 12 is allowed to move relative to the table 48 as much or as little as they need in block 104. In block 106, the ankle detail scan 74 is conducted. It is appreciated that the patient 12 is immobilized relative to the table 48 during acquisition of the ankle detail scan 74 in block 106. Once the ankle detail scan 74 has concluded, if desired, the patient 12 again is free to move relative to the table 48 in block 108. Next, the knee detail scan 78 is performed in block 110. It is appreciated that the patient 12 remain immobilized relative to the table 48 during acquisition of the knee detail scan 78. Once the knee detail scan 78 has concluded in block 110, the patient 12, if desired, is again free to move in block 112. Next, a hip detail scan 82 is performed in block 114. Again, it is appreciated that the patient 12 remain immobilized relative to the table 48 during acquisition of the hip detail scan 82. In block 116, the respective ankle, knee and hip detail scans 74, 78 and 82 are compared to the legend 73 to determine the orientation of the ankle, knee and hip detail scans 74, 78 and 82 with respect to the legend 73. The ankle, knee and hip detail scans 74, 78 and 82 are then compiled in block 118. In block 120, a characteristic of the limb is determined based on the compilation. Again, the characteristic can be any combination of joint or bone characteristics such as a mechanical axis of the leg, the axis of the femur, the axis of the tibia and others.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A method of imaging an extremity of a patient, the method comprising:

securing the patient to a table and restraining the patient to the table;

locating a first, a second and a third anatomical reference area of the extremity corresponding to an ankle, a knee and a hip;

acquiring a first, a second and a third set of image data from the first, second and third anatomical reference areas, respectively while the first, second and third anatomical reference areas are immobilized relative to the table;

compiling the first, second and third sets of image data to produce a map having known positional information of the first, second and third anatomical reference areas relative to each other;

subsequent to the patient moving relative to the table, acquiring a fourth, a fifth and a sixth set of image data of the first, second and third anatomical reference areas of the extremity, respectively, the fourth, the fifth and the sixth sets of image data having increased image information relative to the first, second and third sets of image data, respectively;

correlating locations of the fourth, fifth and sixth sets of image data relative to the first, second and third sets of image data using the map; and determining a characteristic of the extremity based on the correlating.

2. The method of claim 1 wherein acquiring the first, second and third set of image data comprises:
acquiring only ten or less images for each of the first, second and third sets of image data.

3. The method of claim 2 wherein acquiring the first, second and third set of image data comprises:
acquiring only five or less images for each of the first, second and third sets of image data.

4. The method of claim 2 wherein two of the only ten or less images from at least one of the first, second and third sets of image data are planar images on intersecting planes.

5. The method of claim 2, further comprising:
performing a localizer scan on each of the first, second and third anatomical reference areas prior to acquiring the first, second and third sets of image data.

6. The method of claim 2 wherein the fifth set of image data is a bulk image scan of the second anatomical reference area comprising a greater quantity of image scans compared to the second set of image data.

7. The method of claim 6 wherein the fourth and sixth sets of image data each comprise a greater quantity of image scans compared to the first and third sets of image data, respectively.

8. The method of claim 1 wherein the characteristic of the extremity is a mechanical axis of a tibia and femur, respectively, relative to the knee.

9. The method of claim 1, further comprising at least one of:
moving the patient relative to the table between the acquiring of the fourth and fifth set of image data; and
moving the patient relative to the table between the acquiring of the fifth and sixth set of image data.

10. The method of claim 1 wherein acquiring the fifth set of image data comprises using a send/receive imaging coil.

11. A method of imaging an extremity of a patient, the method comprising:
performing a localizer scan on each of an ankle, a knee and a hip;
subsequent to performing the localizer scan, acquiring a first, a second and a third set of image data from the ankle, knee and hip of the extremity, respectively while the extremity is immobilized;
mobilizing the extremity;
compiling the first, second and third sets of image data to produce a map of the extremity, the map having positional information of the ankle, knee and hip relative to each other, wherein each of the first, second and third sets of image data consists of less than five planar images for each of the first, second and third sets of image data;
repositioning the extremity in an immobilized state subsequent to the mobilizing;
acquiring a fourth, a fifth and a sixth set of image data of the ankle, knee and hip, respectively, the fourth, fifth and sixth sets of image data each having more image information relative to the first, second and third sets of image data, respectively;
correlating locations of the fourth, fifth and sixth set of image data relative to the first, second and third sets of image data using the map; and
determining a characteristic of the extremity based on the correlating.

12. The method of claim 11 wherein the fifth set of image data is a bulk image scan of the knee acquired with a send/receive imaging coil.

13. The method of claim 12 wherein the characteristic of the extremity is a mechanical axis of a tibia and femur, respectively, relative to the knee.

14. The method of claim 11, further comprising at least one of:
moving the patient relative to the table between the acquiring of the fourth and fifth set of image data; and
moving the patient relative to the table between the acquiring of the fifth and sixth set of image data.

15. A method of imaging an extremity of a patient, the method comprising:
locating an ankle, knee and hip of the extremity;
securing the patient to a table and restraining the patient to the table, such that the patient's ankle, knee and hip are all immobilized relative to the table;
acquiring a first, second and third set of image data from the ankle, knee and hip, respectively;
compiling the first, second and third sets of image data to produce a legend of the extremity, the legend having known positional information of the ankle, knee and hip relative to each other;
acquiring a fourth image data set of the ankle while the patient is immobilized relative to the table in a first position;
subsequent to the patient moving relative to the table to a second position, acquiring a fifth image data set of the knee while the patient is immobilized in a third position;
subsequent to the patient moving to a fourth position relative to the table, acquiring a sixth image data set of the hip while the patient is immobilized in a fifth position;
correlating locations of the fourth, fifth and sixth sets of image data relative to the first, second and third sets of image data using the legend; and
determining a mechanical axis of a tibia and femur, respectively, relative to the knee based on the correlating.

* * * * *